(12) United States Patent
Bottrell

(10) Patent No.: US 9,395,347 B2
(45) Date of Patent: Jul. 19, 2016

(54) EXPLOSIVE DEVICE DETECTION TOOL

(71) Applicant: Andrew Lee Bottrell, San Diego, CA (US)

(72) Inventor: Andrew Lee Bottrell, San Diego, CA (US)

( * ) Notice: Subject to any disclaimer, the term of this patent is extended or adjusted under 35 U.S.C. 154(b) by 415 days.

(21) Appl. No.: 14/062,686

(22) Filed: Oct. 24, 2013

(65) Prior Publication Data

US 2015/0114144 A1    Apr. 30, 2015

(51) Int. Cl.
*G01N 33/22* (2006.01)

(52) U.S. Cl.
CPC .................... *G01N 33/227* (2013.01)

(58) Field of Classification Search
None
See application file for complete search history.

(56) References Cited

U.S. PATENT DOCUMENTS

| | | | | |
|---|---|---|---|---|
| 2,414,810 A * | 1/1947 | Harris et al. | ................. | 24/11 C |
| 2,654,156 A * | 10/1953 | Boyer | ..................... | G01B 3/28 33/836 |
| 4,526,030 A * | 7/1985 | Vecera, Jr. | ............... | G01B 5/18 33/837 |
| 5,148,704 A * | 9/1992 | Tsai | ....................... | G01L 17/00 340/442 |
| 6,481,034 B2 * | 11/2002 | Elsener et al. | ..................... | 7/118 |
| 7,437,986 B2 * | 10/2008 | Fuss et al. | ....................... | 89/1.13 |
| 7,497,113 B1 * | 3/2009 | Patel | ..................... | G01M 17/02 33/203 |
| 8,220,075 B2 * | 7/2012 | Chen | ......................... | A41B 3/06 2/132 |
| 2010/0307232 A1 * | 12/2010 | Petrucelli | ............... | G01L 17/00 73/146.8 |
| 2011/0247221 A1 * | 10/2011 | Elardo | ............................ | 30/290 |
| 2013/0333119 A1 * | 12/2013 | Maynard | .......................... | 7/163 |

OTHER PUBLICATIONS

George Knives, Mine Probes, available at http://www.georgeknives.com/probes.html.
Gerber: "Basic Mine Probe Kit, Sheath" http://www.gerbergear.com/Military/Gear/Basic-Mine-Probe-Kit_05984 downloaded from wayback machine dated Oct. 20, 2011.

* cited by examiner

*Primary Examiner* — Robert R Raevis
(74) *Attorney, Agent, or Firm* — EIP US LLP

(57) ABSTRACT

Embodiments disclosed herein relate to a Detection Tool for use by personnel tasked with locating Improvised Explosive Devices ("IEDs"). The Detection Tool is preferably constructed of a non-metallic and non-conductive material so as to reduce the risk of accidental triggering of electrical explosive devices. The Detection Tool is shaped in order to penetrate surfaces, such as compacted roadways or other thoroughfares, where IEDs may be concealed. Additionally, the Detection Tool may include measurement indicators as well as attachment means so as to be easily integrated with other gear carried by users of the Detection Tool.

18 Claims, 4 Drawing Sheets

EXPLOSIVE DEVICE DETECTION TOOL

BACKGROUND OF THE INVENTION

Field of the Invention

Improvised Explosive Devices (IEDs) are a scourge of modern warfare. Such devices are essentially homemade bombs with two primary components: an explosive substance and a detonation mechanism. The explosive substance may be a variety of substances, including: conventional explosives (e.g. TNT, Semtex, RDX, and other explosives), unspent munitions (e.g. artillery shells) and other homemade explosives using combustible substances. Similarly, detonation mechanisms can take many forms from the tried-and-true pressure plates to cellular-based remote detonation devices. Due to the myriad ways in which an IED can be constructed and deployed in the field, such devices are inherently difficult to detect and defend against. Unfortunately, for these reasons and others, IEDs are responsible for an increasing percentage of casualties in conflict zones around the world.

Another vexing aspect of IEDs is the ease with which an enemy may covertly deploy them. An IED may be, for example, buried beneath transient objects like trash, built into a structure, or hidden "in plain sight" within common product packaging. One of the most common methods of concealing an IED is to bury it within the ground along a path of travel, such as a sidewalk, roadway or other commonly accessed route. Burying IEDs is a particularly effective method for attacking vehicles and other equipment that are generally confined to existing routes. Moreover, IEDs are particularly easy to conceal in areas where travel routes are typically unpaved paths (e.g. gravel or dirt roads) since alteration of such paths is easy to implement and difficult to detect.

Detection of IEDs may be performed remotely by robotic or other electronic means or manually by Explosive Ordinance Disposal (EOD) personnel or similarly trained professionals. Many innovative electronic means of detecting IEDs, including sensor-laden robots, have been deployed to various conflict zones successfully. On the one hand, such devices have the benefit of advanced sensors and processing technology. And critically, an unsuccessful interception of an IED with a robotic or other electronic device typically does not result in human casualties. However, such devices tend to be heavy, cumbersome and expensive to deploy in a conflict zone. Moreover, their inherent complexity requires special training to use effectively, to repair, and to maintain, which may limit the practicality of such tools in conflict zones.

EOD personnel have also employed various tools to assist with manual detection of IEDs and other dangerous explosive devices. For example, hand-held, electronic metal detection probes have been used for IED and mine clearance missions. Though such probes advantageously provide portable sensing capabilities, such probes also suffer from the requirement to have constant power in order to operate effectively, which requires an EOD or similar personnel to carry batteries. Additionally, such sensing probes tend to be heavy and ungainly themselves due to their size and construction. Finally, such sensing probes may only be able to detect the presence of metallic structures. Generally speaking, EOD and other warfighting personnel prefer tools that are lightweight, easy to carry, and effective for the mission at hand.

Accordingly, there is a need for a tool to assist with the detection of IEDs and other explosive devices that is suitable to the task and not burdensome to the operator.

SUMMARY OF THE INVENTION

Various embodiments described below relate to an improved explosive device detection tool. In one embodiment, a Detection Tool comprises a body section; a tapered section; and a measurement indicator, wherein the detection tool is formed of a non-metallic, non-conductive and non-sparking material. The Detection Tool may further comprise means for attaching the detection tool to a user or to equipment. For example, the attachment means may comprise a clip or a lanyard. The Detection Tool may include a non-metallic and non-conductive material that is one of: glass-cloth reinforced epoxy, thermoplastic acrylic-polyvinyl chloride, or ABS. Alternatively, the Detection Tool may include a non-metallic and non-conductive material that is one of: G10, G11, FR4, FR5, Kydex® plastic or ABS plastic. The Detection Tool may include measurement indicator comprising: a marking, depression, groove, channel, slot, ridge, or hole. The Detection Tool may comprise a body section that has an octagonal cross-section. The Detection Tool may further comprise a tapered section that has an octagonal cross-section. In some embodiments, the Detection Tool comprises a length of the body section that is longer than a length of the tapered section. In some embodiments, the Detection Tool further comprises a body section further including a surface texture. In some embodiments, the surface texture is at least one of: hatching, cross-hatching, knurling, stippling, dimpling, or checkering. Finally, the Detection Tool may comprise a non-metallic and non-conductive material that is also non-magnetic.

DETAILED DESCRIPTION OF CERTAIN INVENTIVE EMBODIMENTS

Figure 1:
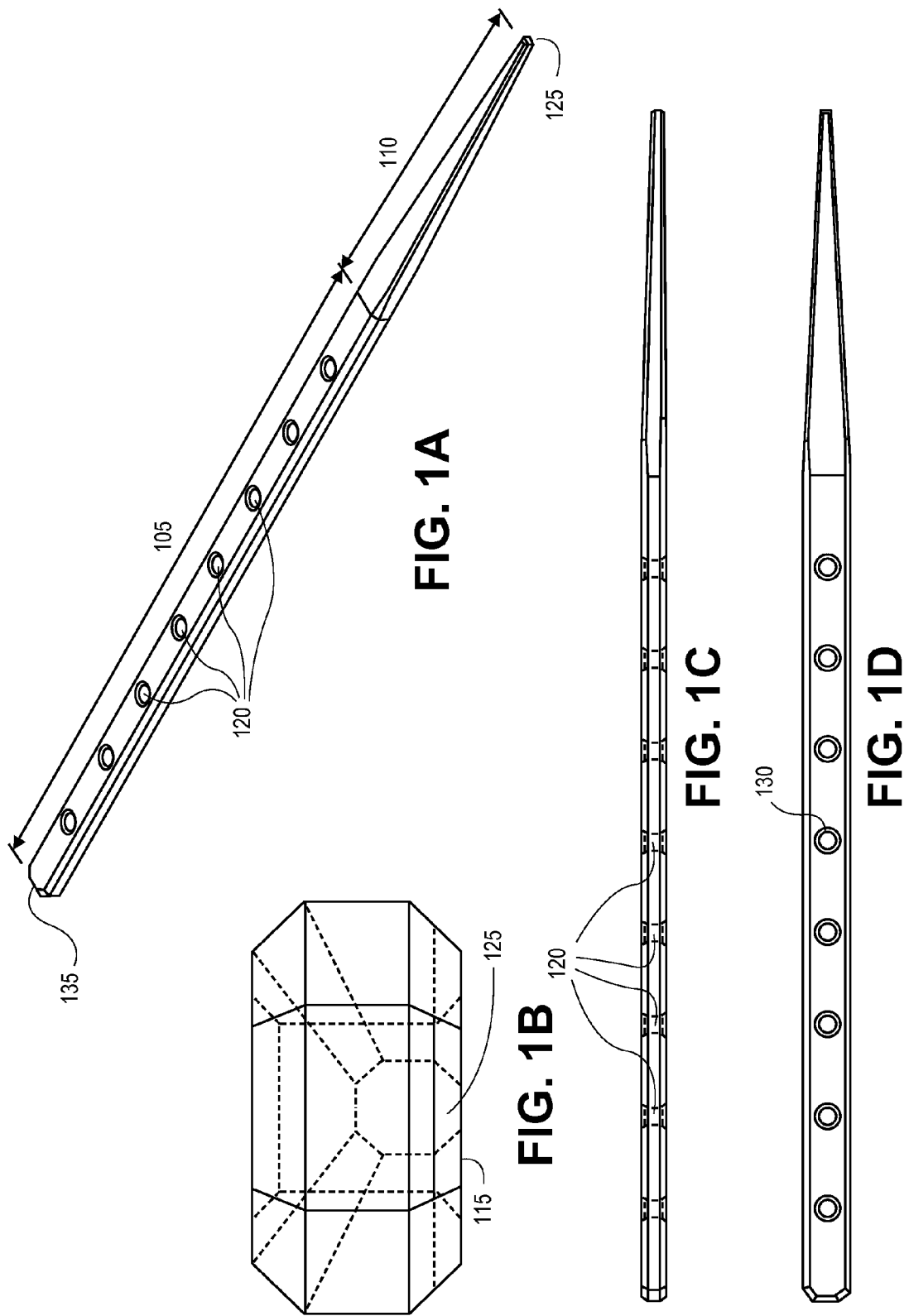
FIG. 1A is an isometric view of an example of a Detection Tool according to one or more embodiments.
FIG. 1B is a cross-sectional view of the Detection Tool from FIG. 1A according to one or more embodiments.
FIGS. 1C and 1D are planar views of the Detection Tool from the side and top, respectively.

Embodiments disclosed herein provides an Improvised Explosive Device Detection Tool ("Detection Tool") for use by EOD and other personnel for the detection of IEDs, mines and other explosive devices. The Detection Tool may include a body section and a tapered section made of a non-magnetic, non-ferrous, non-sparking, non-metallic and non-conductive material. Additionally, the Detection Tool may further include length indicators along the body section.

The manual detection of IEDs and other explosive devices by EOD and other personnel may involve probing items, structures and surfaces suspected of being, housing or concealing explosives. A common task of an EOD professional in this regard is to probe compacted surfaces such as dirt or gravel pathways where a suspected IED is buried or otherwise concealed. Devices such as IEDs may be sensitive to contact with metal or merely the presence of metal. For example, an IED may use a trigger that is sensitive to the touch or presence of metal through a magnetic or capacitive switch. Or, more simply, an IED may be triggered by a short caused when a conductive probe comes in contact with electrical components of the detonation mechanism. In any event, it is generally better to have a Detection Tool made from a material that is strong enough to probe various compacted materials (e.g., dirt or gravel), but unlikely to trigger an IED or other explosive upon contact with such a device.

In some embodiments, the Detection Tool may comprise materials having one or more of the following characteristics: strong, lightweight, flexible, water-proof, non-magnetic, non-ferrous, non-sparking, non-metallic and non-conductive. Examples of such materials include glass-cloth reinforced epoxy based materials such as G10, G11, FR4 and FR5. Such materials have many advantageous properties, including dimensional stability, high mechanical strength, low water absorption, and extreme electrical insulation. Additionally, certain versions of these glass-cloth reinforced epoxy based materials are advantageously fire resistant. Other materials such as thermoplastic acrylic-polyvinyl chloride materials (e.g. Kydex®) and acrylonitrile butadiene styrene (ABS) plastics offer similar advantageous qualities. It will be appreciated by a skilled artisan that the aforementioned materials are only exemplary, and that any material exhibiting advantageous properties such as those described above are equally suitable.

Detection Tools may include two distinct sections: a body section and a tapered section. Notably, though described as two distinct sections for the purposes of uniquely identifying each, these two sections may be each part of an integrally formed body. The body section and tapered section of a Detection Tool may be of any length that suits the particular personnel using the tool. In certain embodiments, the body section is between 4 and 12 inches in length and the tapered section is between 1 and 5 inches in length.

The body section of a Detection Tool may be formed in any particular cross-sectional shape, including square, polygonal, round, elliptical or mixtures of the same. In certain embodiments, the body section has a square or octagonal cross-section.

The body section may also include measurement indicators, which may be markings, depressions, grooves, channels, slots, ridges, holes, prints, combinations of these or other indications on the body section. The measurement indicators may be on one or more sides of the body section. Typically, the measurement indicators are separated by standard units of length, such as one inch or one centimeter. In some embodiments, textual references such as numeric units may be placed on the body section for additional reference. Additionally, the length between the blunt end of the Detection Tool and the first measurement indicator may be of the same standard length.

A Detection Tool comprising measurement indicators may be used in the field, for example, as a size reference for photographic documentation of evidence. Similarly, the measurement indicators may be used to measure the depth or penetration of the Detection Tool into a surface, such as a compacted gravel roadway. In some embodiments, the measurement indicators may also provide a user with tactile feedback, and may provide better grip for usage of the Detection Tool. An additional benefit of certain embodiments of measurement indicators, such as holes, is a reduction in weight of the Device Tool.

The surfaces of the body section may be provided with a surface texture to enhance the grip of the Detection Tool in use and in storage. For example, the surface of the body section may include hatching, cross-hatching, knurling, stippling, dimpling, checkering or other texturing. The surface texture may be formed integrally with the material of the Detection Tool, or may be applied separately to the Detection Tool. For example, a Detection Tool may be milled with appropriate tools to include appropriately textured surfaces. Alternatively, a surface treatment, such as a rubberized coating, may be applied to a Detection Tool to further enhance its grip and electrically insulative and/or non-conductive properties.

Like the body section, the tapered section of a Detection Tool may also be formed in any particular cross-sectional shape, including square, polygonal, round, elliptical or mixtures of the same. In certain embodiments, the tapered section has a square or octagonal cross-section. The tapered section of the Detection Tool facilitates penetration into surfaces, such as compacted or other loose surfaces. For example, the tapered section will penetrate compacted soil more easily than a non-tapered surface. This is advantageous in that it lets the user probe more easily and with less force so that in the event that an IED or other explosive device is contacted, it is contacted with the minimal possible force. In some embodiments, the tapered section may include measurement indicators or surface texture (or both) as described above.

Embodiments of a Detection Tool may be provided with an attachment means such as a lanyard or clip for attaching the Detection Tool to a user or to user equipment. In the case of a lanyard, a material such as fabric, rubber, plastic, mesh or any other suitable material may be attached to the Detection Tool by threading such material through a hole or affixing it to the body section by glue, rivet, staple, or by other means as are known by a skilled artisan. The lanyard may be used to wrap around a user's body part (e.g. wrist) or to attach to existing equipment (e.g., a carabineer). In some embodiments, a measurement indicator, such as a hole through the body section, may also be used as an attachment point for the lanyard.

In the case of a clip, a non-conductive material such as plastic or rubber may be used. Alternatively, metal may be used. In some embodiments, the clip is flexible to allow for attachment of the Detection Tool to surfaces of different size and shape. In certain embodiments, the clip may be integrally formed with the body section, while in others the clip may be attached to the body section by glue, rivet, staple, screw, retainer or some other attachment mechanism. In other embodiments, the clip may attach to the body section at a measurement indicator, such as a hole.

The Detection Tool may be any particular color. For example, the color of the Detection Tool may be the natural color of the material used to form the tool, or the color may be applied separately to the tool. For example, the tool may be colored in a camouflage pattern to match other equipment carried by personnel carrying the Detection Tool. In certain embodiments, a surface texture applied to the Detection Tool also colors the Detection Tool.

The Detection Tool may be configured to work with other personnel equipment. For example, Modular Lightweight Load-carrying Equipment ("MOLLE") is frequently used in the field to carry equipment. Personnel such as EOD personnel may use MOLLE to store and carry a wide variety of tools and other field necessities. Preferably, the Detection Tool is formed in a shape and dimension suitable for use with MOLLE equipment, or other fast attach and detach tactical equipment. Additionally, enhancements such as surface texture and attachment means (e.g. clips or lanyards) may additionally make the Detection Tool easier to carry with existing equipment by preventing the Detection Tool from slipping out of place.

The Detection Tool may be manufactured, based on the material or materials used, by methods known to skilled artisans. For example, ABS and other thermoplastics may be injection molded into molds or other tooling. Reinforced epoxy based materials may first be formed then finished into a Detection Tool using known manufacturing techniques such as milling, sanding, grinding, drilling, pressing, cutting, and the like. Additionally, a Detection Tool may be created in a wide variety of materials by rapid manufacturing methods, such as three-dimensional printing by stereo lithography, selective laser sintering, fused deposition modeling and other known techniques.

FIG. 1A depicts an isometric view of a Detection Tool 100 according to one inventive embodiment. The Detection Tool 100 includes a body section 105 and a tapered section 110. In this embodiment, the body section 105 is nine inches long and the tapered section 110 is four inches long, for a total length of thirteen inches. Additionally, the body section 105 is one-quarter of an inch tall and one-half of an inch wide. As discussed above, Detection Tool 100 can be formed to a variety of dimensions based on preferences of a user. For example, a user may prefer to carry one longer Detection Tool and one shorter Detection Tool for use in different scenarios.

Detection Tool 100 includes a generally octagonal cross-section for both the body section 105 and tapered section 110 in this particular embodiment. Further, in this embodiment the tapered section 110 tapers in such a fashion that a long side 115 of Detection Tool 100 is flat (or planar) across the entire length of the tool. The long side 115 allows a user to manipulate the Detection Tool 100 smoothly using a consistent reference and helps the Detection Tool 100 to rest firmly against flat surfaces within carrying equipment, such as MOLLE.

Detection Tool 100 includes holes 120 (measurement indicators) along the length of body section 105. The holes 120 (measurement indicators) may serve multiple purposes. First, in this embodiment, the holes 120 (measurement indicators) are spaced in standard lengths of one inch between each indicator (hole). Additionally, the distance between blunt end 135 and the first hole (measurement indicator) is the same standard length. Second, the holes 120 (measurement indicators) reduce the mass of the Detection Tool 100. Third, the holes 120 (measurement indicators) provide tactile feedback to a user. For example, a user can manipulate the Detection Tool 100 by gripping a hole 120 with a finger and sliding the Detection Tool 100 forward or backward. In this embodiment, the holes 120 (measurement indicators) include chamfered edges to increase the tactile feedback and further reduce weight.

The Detection Tool 100 shown in FIG. 1 also includes a tapered section 110 that extends from the body section 105 to a tapered end 125. In this embodiment, the degree of tapering of tapered section 110 is approximately 2.5 degrees; however, the degree of tapering may easily be conformed to user preferences. In this embodiment, the tapered end 125 is an octagonal plane rather than a point. In some cases, a user of may prefer that the tapered end 125 not be a sharp point due to the possibility of piercing a dangerous device, such as a chemical dispersion device, while probing. However, in other embodiments the tapered end 125 may come to a point.

FIG. 1B depicts a cross-sectional view of the Detection Tool 100 according to one inventive embodiment. As described above in connection with FIG. 1A, the Detection Tool 100 may include a body section 105, a tapered section 110, a long side 115, a measurement indicators 120, and a tapered end 125. This cross-sectional view of the Detection Tool 100 shows the tapering while maintaining long side 115 as a consistent reference. Notably, in other embodiments, the tapered end 125 may instead be centered about the long axis of the Detection Tool 100.

FIG. 1C depicts a planar view of the side of Detection Tool 100. In this view, a series of holes 120 (measurement indicators) can be seen in broken lines extending from one side of Detection Tool 100 to the other. FIG. 1D depicts a planar view of the top of the Detection Tool 100. In this view, the holes 120 (which may serve as measurement indicators) can be seen with chamfering 130 around the edges.

Figure 2:
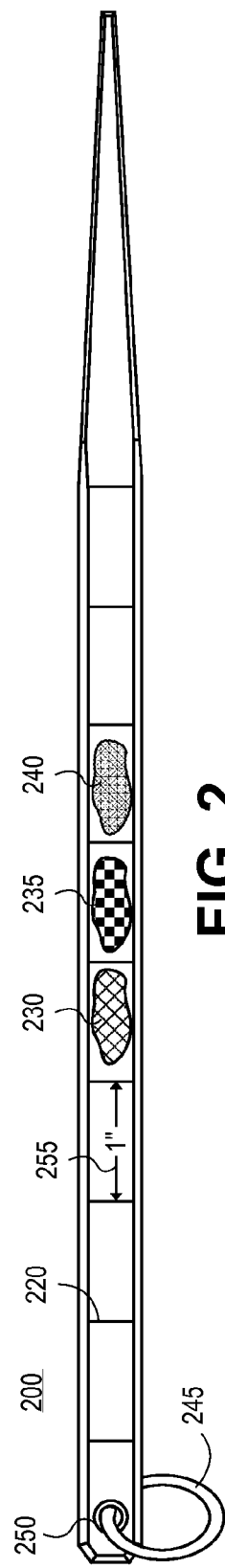
FIG. 2 is a planar view of a Detection Tool from the top having optional features according to one or more embodiments.

Turning now to FIG. 2, a planar view of a Detection Tool 200 having optional features is provided. In this example, the Detection Tool 200 includes hatch lines 220 as measurement indicators along the length of body section 205. The Detection Tool 200 also depicts three different optional surface textures 230, 235 and 240. As shown, surface texture 230 is a cross-hatch type of surface texture that may add grip and tactile feedback when using Detection Tool 200. Surface texture 235 is a checkered surface that may similarly add grip and tactile feedback when using Detection Tool 200. Finally, surface texture 240 is a knurled surface texture that may likewise add grip and tactile feedback when using the Detection Tool 200. Notably, while the surface textures 230, 235, and 240 are each shown covering only a small portion of body section 205, it should be understood that such surface textures can be formed across any portion of Detection Tool 200, including, for example, the entire body section.

Detection Tool 200 is also depicted with a lanyard 245. In this embodiment, the lanyard 245 is attached to the Detection Tool 200 by running the lanyard through an attachment hole 250. In this specific embodiment, the attachment hole 250 is not a measurement indicator. However, in other embodiments a hole acting as a measurement indicator could also be an attachment point for lanyard 245. Detection Tool 200 is additionally depicted with a text reference 255. The text reference 255 may indicate the length between hatch lines (measurement indicators) 220.

Figure 3A:
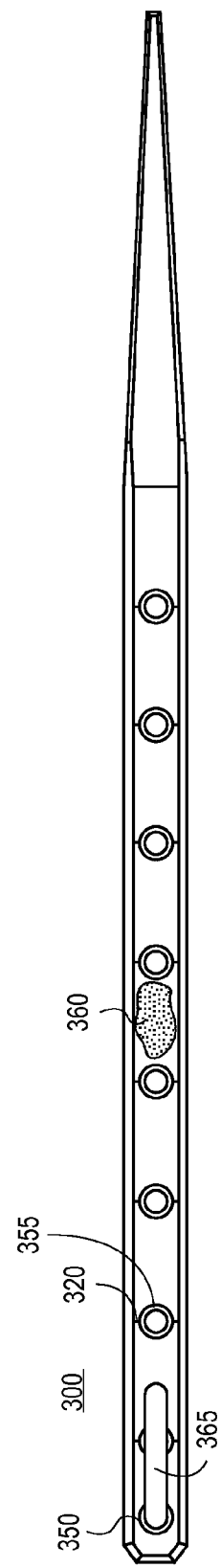
FIGS. 3A and 3B are planar views of another embodiment of a Detection Tool from the top and side with an optional clip.
Figure 3B:

FIGS. 3A and 3B depict planar views of a Detection Tool 300 from the top and side with additional optional features. In this example, Detection Tool 300 includes hatch lines 320 and holes 355 as measurement indicators. In this embodiment, the hatch lines 320 and holes 355 (measurement indicators) are combined to provide even more conspicuous measurement indication while also advantageously reducing the weight of Detection Tool 300. Detection Tool 300 is also depicted with yet another form of surface texturing, stippling 360. As discussed above, the stippling 360 may be applied to any amount of the Detection Tool 300, including, for example, the entire body section.

Detection Tool 300 also may include clip 365. In this embodiment, clip 365 is attached to attachment hole 350 and may be removed easily from the Detection Tool 300. In other embodiments, the clip 365 may be permanently affixed to Detection Tool 300.

Figure 4:
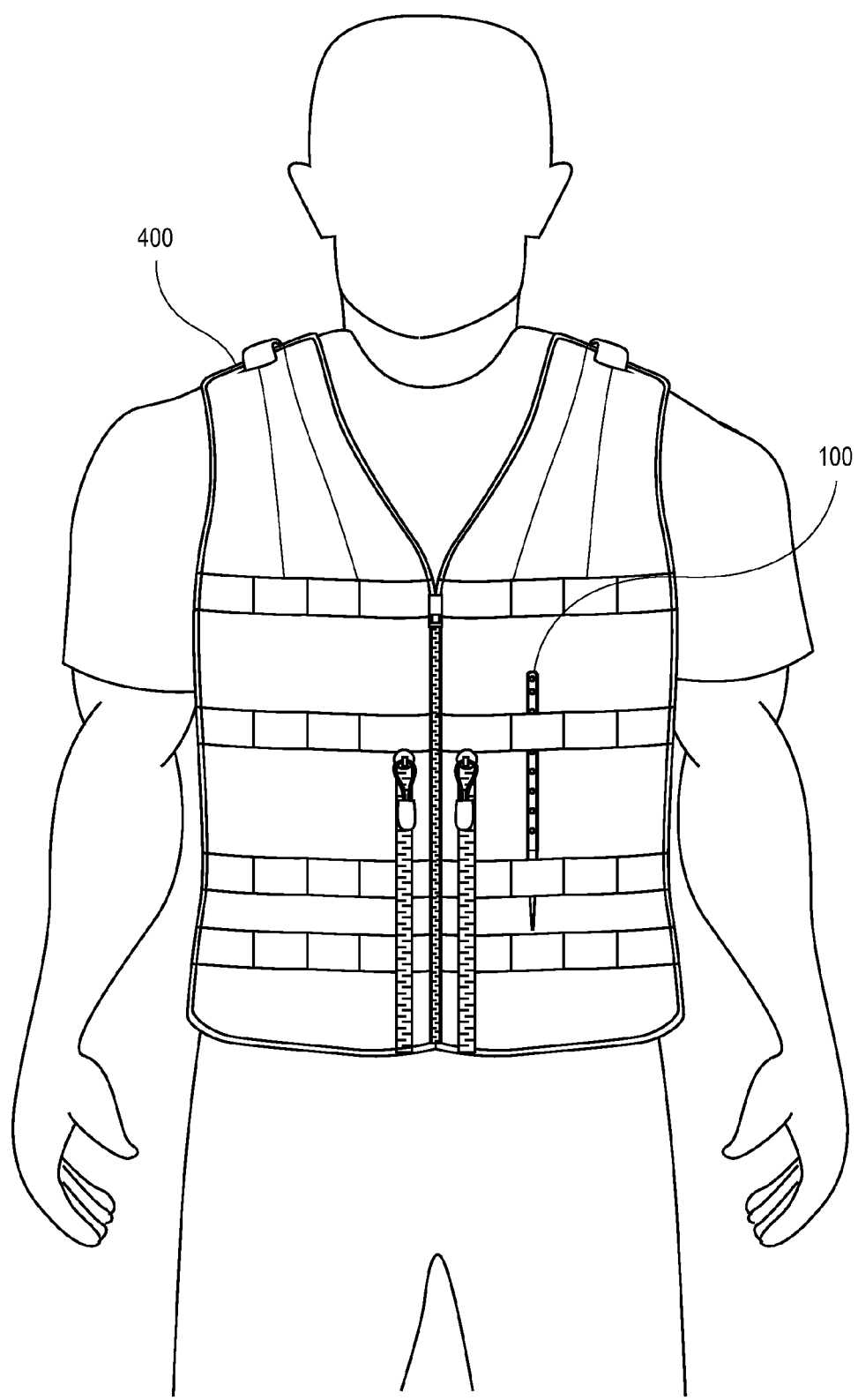
FIG. 4 depicts a Detection Tool stored in a MOLLE vest.

FIG. 4 depicts a Detection Tool, such as Detection Tool 100 stored in personnel equipment 400. The personnel equipment 400 could be, for example, a MOLLE vest worn by EOD personnel. As shown, the Detection Tool 100 slides easily and securely into the straps on personal equipment 400. One or more surface treatments (not depicted), such as those described above, may create additional grip between Detection Tool 100 and vest 400 so as to prevent the Detection Tool from sliding out of place during movement of the personnel wearing vest 400.

Figure 5:
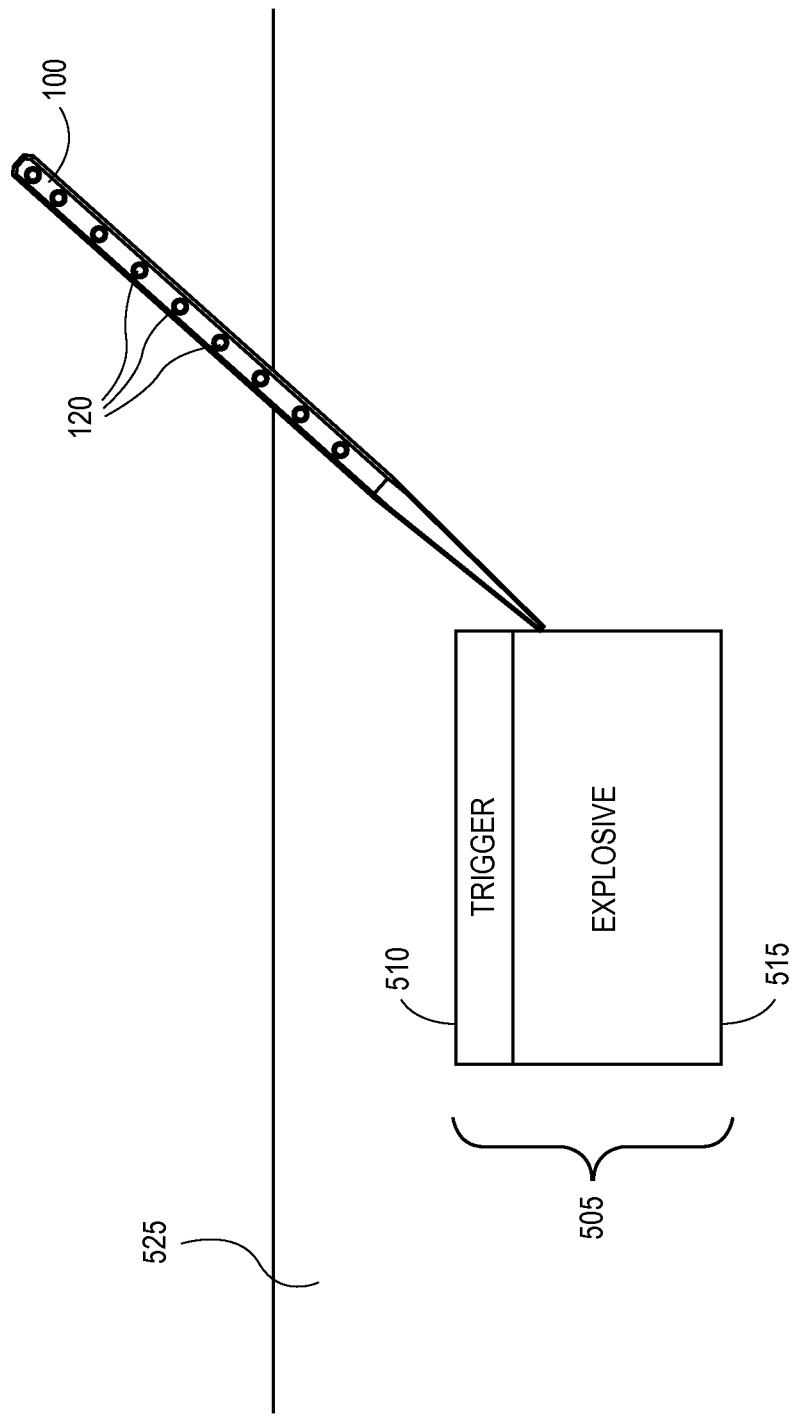
FIG. 5 depicts a Detection Tool in use.

Turning now to FIG. 5, a Detection Tool 100 is shown in use. In this example, the Detection Tool 100 is depicted penetrating compacted surface 525, which may be, for example, dirt, gravel, a loose road surface, or other types of penetrable surfaces. The Detection Tool 100 is used to probe below surface 525 for IEDs or other devices of interest. As can be seen, Detection Tool 100 has impacted IED 505, which includes trigger 510 and explosive 515. As can also be seen, holes 120 give an indication of the depth of IED 505. Additionally, if IED 505 were to be recovered intact, holes 120 (measurement indicators) could be used as a size reference for photographic evidence when placed adjacent to IED 505.

Throughout the foregoing description, numerous specific details were set forth in order to provide a thorough understanding of the invention. It will be apparent, however, to one of ordinary skill in the art, that the invention may be practiced without some of these specific details or with modifications to the same. Accordingly, the scope and spirit of the invention should be judged in terms of the claims which follow.

What is claimed is:

1. A detection tool, comprising:
   a body section comprising a length and a polygonal cross-section having at least four sides;
   a tapered section connected to the body section and comprising a length and an octagonal cross-section, the length of the tapered section being coaxial with the length of the body section; and
   a plurality of measurement indicators on the body section, the measurement indicators arranged along the length of the body section,
   wherein the body section and the tapered section are formed of a non-metallic and non-conductive material.

2. The detection tool of claim 1, further comprising means for attaching the detection tool to a user or to equipment.

3. The detection tool of claim 2, wherein the attachment means comprises a clip.

4. The detection tool of claim 2, wherein the attachment means comprises a lanyard.

5. The detection tool of claim 1, wherein the non-metallic and non-conductive material comprises thermoplastic acrylic-polyvinyl chloride.

6. The detection tool of claim 1, wherein the plurality of measurement indicators comprise a plurality of apertures extending from a first side of the body section to a second side of the body section.

7. The detection tool of claim 1, wherein the body section has an octagonal cross-section.

8. The detection tool of claim 1, wherein the length of the body section is longer than the length of the tapered section.

9. The detection tool of claim 8, wherein the length of the body section is between 4 to 12 inches.

10. The detection tool of claim 9, wherein the length of the tapered section is between 1 to 5 inches.

11. The detection tool of claim 1, wherein the body section further comprises a surface texture.

12. The detection tool of claim 11, wherein the surface texture is at least one of: hatching, cross-hatching, knurling, stippling, dimpling, or checkering.

13. The detection tool of claim 1, wherein the non-metallic and non-conductive material is non-magnetic.

14. the detection tool of claim 1, wherein the tapered section comprises a first end connected to the body section and a second end comprising a point.

15. the detection tool of claim 1, wherein the tapered section comprises a first end connected to the body section and a second end comprising a tapered end.

16. The detection tool of claim 1, wherein the non-metallic and non-conductive material comprises glass cloth reinforced epoxy.

17. The detection tool of claim 1, wherein the non-metallic and non-conductive material comprises ABS plastic.

18. The detection tool of claim 1, wherein the body section comprises a first side co-planar with a first side of the tapered section, and wherein the first side of the body section and the first side of the tapered section are flat across an overall length of the detection tool.

* * * * *